(12) United States Patent
Corless

(10) Patent No.: US 6,545,695 B1
(45) Date of Patent: Apr. 8, 2003

(54) APPARATUS FOR LOCATING A PLURALITY OF ARTICLES

(75) Inventor: Anthony Robert Corless, Ash (GB)

(73) Assignee: Central Research Laboratories Limited, Middlesex (GB)

( * ) Notice: Subject to any disclaimer, the term of this patent is extended or adjusted under 35 U.S.C. 154(b) by 0 days.

(21) Appl. No.: 09/674,414

(22) PCT Filed: May 4, 1999

(86) PCT No.: PCT/GB99/01372

§ 371 (c)(1),
(2), (4) Date: Dec. 19, 2000

(87) PCT Pub. No.: WO99/56866

PCT Pub. Date: Nov. 11, 1999

(30) Foreign Application Priority Data

May 1, 1998 (GB) .............................................. 9809265

(51) Int. Cl.[7] .............................................. B41J 2/435
(52) U.S. Cl. ....................................................... 347/224
(58) Field of Search ................................ 347/224, 225, 347/263; 257/741; 219/121.68; 198/377.06; 222/590; 435/309.1

(56) References Cited

U.S. PATENT DOCUMENTS

| | | | | |
|---|---|---|---|---|
| 4,707,722 A | * | 11/1987 | Folk et al. .................. | 257/741 |
| 4,754,900 A | * | 7/1988 | MacKay ...................... | 222/590 |
| 5,305,867 A | * | 4/1994 | Leaton .................. | 198/377.06 |
| 5,506,141 A | * | 4/1996 | Weinreb et al. .......... | 435/309.1 |
| 5,897,797 A | * | 4/1999 | Drouillard et al. ..... | 219/121.68 |
| 6,180,914 B1 | * | 1/2002 | Jones et al. ............ | 219/121.68 |

FOREIGN PATENT DOCUMENTS

EP 0 131 182 A1 * 6/1984 ............. B05B/5/02

* cited by examiner

Primary Examiner—Hai Pham
(74) Attorney, Agent, or Firm—Martin Fleit; Paul D. Bianco; Fleit Kain Gibbons Gutman & Bongini, P.L.

(57) ABSTRACT

An apparatus for locating a plurality of articles for laser marking comprising a support plate (16) having a plurality of apertures (18) extending from a first surface of the plate (15) to a second surface of the plate (17). The apertures are dimensioned to receive said articles (12) at the first surface of the plate (15), so that the at least a portion of the article is exposed through the aperture (18). Preferably apertures are defined by tapering walls.

In use a laser (30) is directed towards a protruding portion of the article (21). The extent to which the articles protrude through the aperture (18) is significantly less than the variation in diameter of articles (12) to be laser marked. This eliminates the need for the laser to focus on individual articles (12).

16 Claims, 2 Drawing Sheets

APPARATUS FOR LOCATING A PLURALITY OF ARTICLES

FIELD OF THE INVENTION

This invention relates to an apparatus for locating a plurality of articles, more particularly but not exclusively the articles are located for laser marking; markable articles are used for example in combinatorial chemistry.

BACKGROUND OF THE INVENTION

Combinatorial chemistry is a technique whereby very many different chemical compounds are produced by multiple chemical reactions. Articles (commonly known as beads) of the size approximately of a tenth of a millimeter (mm) in diameter are typically used in such reactions. Molecules can be attached to the articles by way of chemical bonds sometimes called 'hooks'.

To form a library of chemical reagents, it is usual to start with a large number of articles. In order to illustrate a combinatorial process, it is useful to consider the following example. Articles are divided into 3 groups. A different reagent (A, B or C) is then be added to each group of articles. There are now 3 types of molecules attached to the articles: articles in group 1 have molecules of reagent A attached to them, articles in group 2 have molecules of reagent B, and articles in group 3 have molecules of reagent C. Next, the 3 groups of articles are pooled, mixed up, and again split up into 3 groups. Three more separate reactions are then carried out. This results in a combination of 3 reactions in the first stage of the process, and 3 reactions in the second stage, producing 9 different species of molecule. If the groups of articles are again pooled, mixed up, and split up into 3 further groups, 27 different compounds are generated.

The library of compounds created by the above steps is known as a 3×3×3 library. Nine individual (3+3+3) reactions have been carried out, and 27 (3×3×3) different compounds have been generated. Other sizes of library may be created by varying the number of reaction or synthesis stages, and by varying the number of groups of articles.

Laser marking is used as a method of tracking the articles in the above mentioned combinatorial synthesis. In previous methods of laser marking, each article was placed on a flat surface. A laser beam was applied to an upper surface of the article, which was typically spherical or close to spherical, such as an oblate sphere. This method relied on the laser beam focussing on each article to be ablated so as to achieve marking. Since the spherical articles were often of varying sizes, considerable effort and time was expended in focusing on each bead before leaser marking could occur. Accordingly the method produced labelled articles but did not result in a very high throughput.

United Kingdom Patent Application BG 2 306 484 (University of Hertfordshire) discloses a machine readable code for use in combinational chemistry techniques. The code may include pits, holes, hollows or grooves.

It is an object of the present invention to alleviate the aforementioned problem.

SUMMARY OF THE INVENTION

According to the present invention there is provided an apparatus for locating a plurality of articles comprising: a support plate having apertures extending from a first surface of the plate to a second surface of the plate, the aperture(s) being dimensioned to receive said article(s) from the first surface so that at least a portion of the article is presented to be viewed from the second surface of the plate; characterised in that the diameter of each aperture is less than 200 $\mu$m.

By selecting the diameter of the aperture especially of the aperture of a first surface and thickness of the support plate, the extent to which spherical articles protrude through the first surface of the support plate is significantly less than the variation in diameter of the articles to be marked. By using this apparatus, spherical articles can be marked more efficiently without the laser having to re-focus on individual spherical articles. The throughput for marking spherical articles is therefore greatly improved.

The protrusion of the spherical article (or bead), through the aperture on the first surface, can be represented by the formula:

$$r(1-\sin(\theta)).$$

where r is the article (or bead) radius and where r.cos$(\theta)=\omega/2$ where $\omega$ is the diameter of the aperture and $\theta$ is the angle enclosed between an intersecting radius and line defining a segment, the point which the sphere touches an edge of an aperture.

There is a simple relationship between the article protrusion (d), the article radius (r), and the diameter of the aperture($\omega$). This is illustrated diagrammatically in FIG. 4.

$\alpha$=sidewall angle $\alpha>\theta$ very bad, bead sits on wall $\alpha=\theta$ apparantly ideal $\alpha>\theta$ line contact assured say $\alpha$=critical contact for 10% undersize bead for standard bead we have r cos $\theta=\omega/2$.

for undersize bead 0–g r cos $\alpha=\omega/2$ 0.9 r cos $\alpha$=r cos $\theta$ $$= \alpha = \cos^{-1}\left(\frac{\cos\theta}{0.9}\right)$$

Generally if beads are from $$Ar_n \leq r \leq br_a \ (a\leq 1, b\geq 1)$$

$$\alpha \leq \cos^{-1}\left(\frac{\cos\theta}{a}\right)$$

For example: the diameters of articles may vary by ±10%. The apertures in the support plate may vary by 5%; through sophisticated fabrication techniques render variation plate apertures negligible. Assuming the articles have a nominal diameter of 300 $\mu$m and the apertures in the support plate are of 100 $\mu$m diameter; if a flat surface is used to support the articles, the change in article height would be 30 $\mu$m, i.e. ±10%, for a ±10% diameter range. However, when an article is located in an aperture, the variation in the protrusion of the article is only ±2 $\mu$m, i.e. <1%.

The apertures in the first surface are preferably dimensioned so that substantially similar projections of spherical articles protrude through the aperture. The apertures optionally comprise side walls which are substantially tapered. The tapering of the side walls restricts the movement of the spherical articles to be marked or ablated.

In an alternative embodiment, in use, spherical articles are disposed between the support plate and a deformable layer. The deformable layer is positioned so as to restrict the movement of the articles which are subsequently ablated so as to achieve marking.

Most preferably a force is applied to the deformable layer further restricting movement of the spherical articles and maintaining the articles uniformly in the apertures. The force may be applied to the upper surface of the layer.

The support plate is preferably planar. The diameter of apertures are preferably less than 100 µm and most preferably less than 50 µm. By limiting the diameter of the apertures within the support plate variable sized spherical articles can be received within the apertures so that at least a portion of the article is visible from the other side of the support plate.

In a further alternative embodiment there is provided an apparatus for locating a plurality of spherical articles which includes the features of the first embodiment and further comprises a placement means for placing articles onto the support surface, the surface being displaceable with respect to the placement means and a discharging means for releasing or ejecting the articles at a predetermined instant.

The discharging means preferably comprises an air jet so that articles can be removed efficiently from the support plate after the laser has marked the articles. Other means of discharging the spherical articles from the support plate may include any of: a vacuum, magnetic, electrostatic device or a mechanical grabber.

In a yet further embodiment there is provided an apparatus for locating a plurality of articles including the features of the first mentioned embodiment and further comprising: a conveyor for displacing the surface with respect to the placement means. Preferably a collector is also provided to recover the articles when they have been removed from the support plate.

BRIEF DESCRIPTION OF THE DRAWINGS

Embodiments of the invention will now be described, by way of example only, and with reference to the Figures in which.

DETAILED DESCRIPTION OF THE INVENTION

Figure 1:
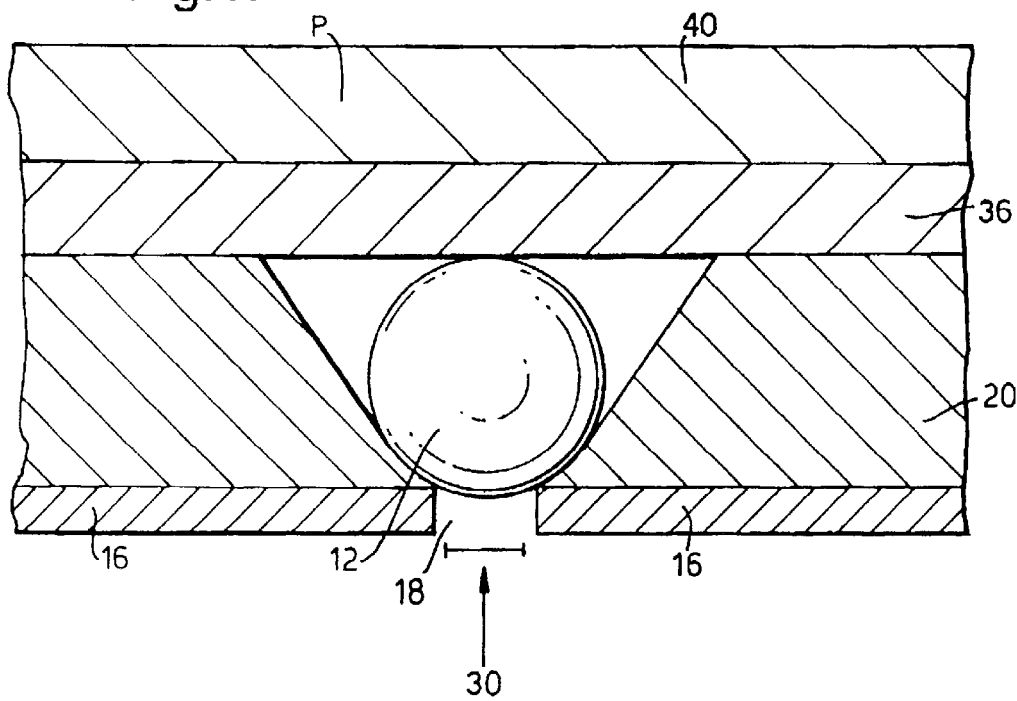
FIG. 1 shows cross-sectional, diagrammatic view of an apparatus for locating a plurality of articles.

Referring to the Figures, FIG. 1 shows a cross-sectional view of an apparatus for locating a plurality of spherical articles 12 comprising a support surface 16 which has a plurality of apertures 18. Each aperture 18 is of known diameter. Articles 12 are placed on the support surface 16 and located in the aperture 18, so that a portion of the article 12 protrudes above the support surface 16. A laser beam 30 marks the portion of each article 12 which protrudes through the aperture 18, with a code. Angular side walls 20 support articles 12 by limiting their movement. A deformable layer 36 and pressurised bag 40 are situated so that the articles 12 are 'sandwiched' between the first surface of the support plate 16 and deformable layer 36, so as to further restrict them before and during laser marking.

Figure 2:
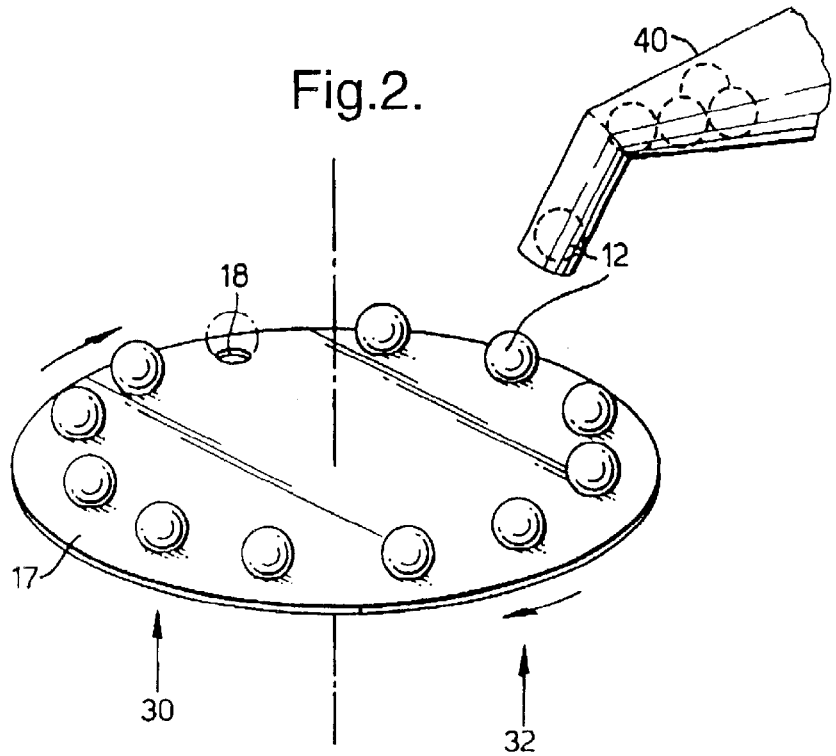
FIG. 2 shows a diagrammatic view of an alternative apparatus having a carousel.

FIG. 2 shows a diagrammatic view of a carousel 17 for locating a plurality of spherical articles 12. Carousel 17 comprises a support plate 16 having a plurality of apertures 18. There is provided a means for placing the articles 12 onto the support plate 16, so that at least a portion of the articles 121 project through the apertures 18. The support plate 16 is displacable with respect to the placing means 40. In use a laser 30 is directed towards the portion of article 12 which can be viewed from the other side of the support plate 16. A means for discharging the spherical articles 32 after laser marking is provided, for example an air jet 32 which is activated at a predetermined instant by way of a detector and controller (not shown).

Figure 3:
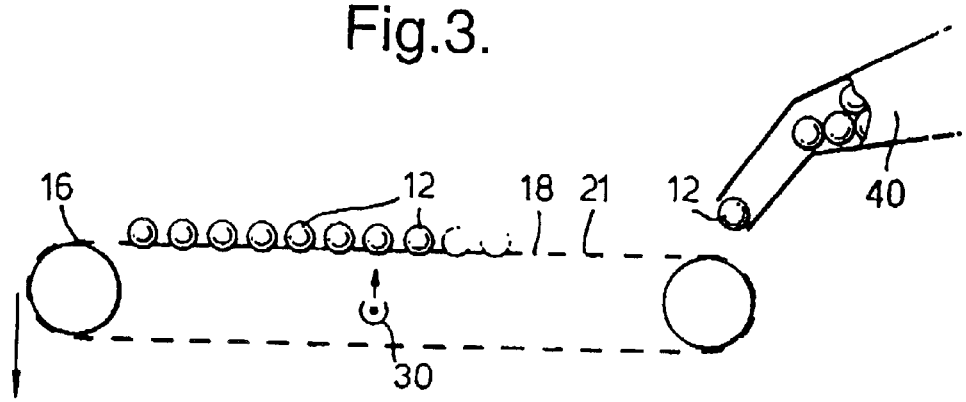
FIG. 3 shows a diagrammatic view of a further alternative apparatus having a conveyor means.

FIG. 3 shows a diagrammatic view of a conveyor surface 21 for locating a plurality of spherical articles 12. Support plate 16 has a plurality of apertures 18. There is provided a placing means for placing the articles 12 onto the support plate 16, so that at least a portion of the articles 12 are received within the apertures 18. The support plate 16 may be displaced with respect to the placing means 40. A laser 30 is directed towards the portion of spherical article 12 which can be viewed from an opposite side of the support plate 16 on which articles are placed. The collection means is situated in order to receive marked spherical articles 12 after they have dropped from conveyor surface 21.

Figure 4:
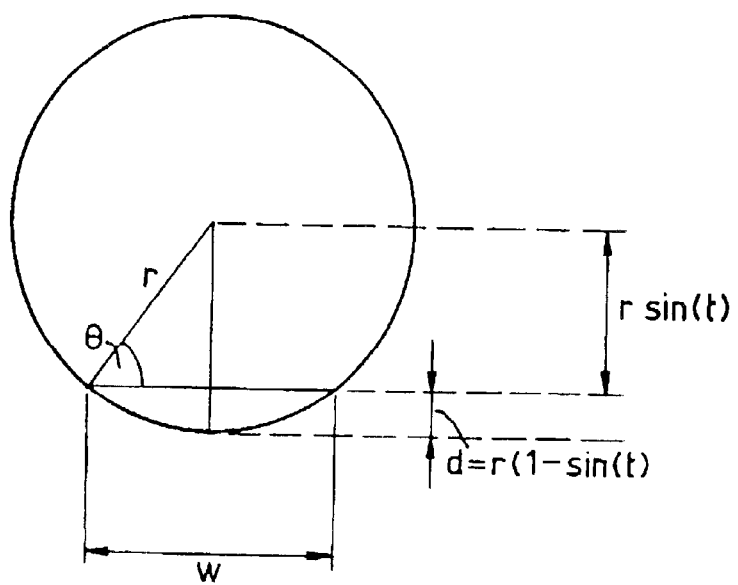
FIG. 4 shows diagrammatically the geometrical relationship between the amount of protrusion of an article, the radius of the article and the diameter of an aperture locating the article.

FIG. 4 shows diagrammatically the mathematical and geometrical relationship between the protrusion of an article (d), the radius of the article (r) and the diameter of an aperture (ω).

A number of possible sizes of bead and aperture appear in the attached Table. The column headed "Figure of merit" gives the ratio of the variation in bead diameter across an allowed range, to the variation in height of the markable portion of the bead which is viewable from the opposite side of the support plate.

There is a strong increase in precision of position with smaller apertures. However, the area available for marking also decreases rapidly, requiring smaller marks, hence greater demands on focussing. Therefore the aperture should not be too small unless the code is very simple.

The example below uses a region of 5×5 dots in a grid on a 10 micron pitch. The overall grid is 50 µm square, therefore an aperture of at least 71 micron diameter is required.

Assume the beads are around 300 µm in diameter with a ±10% variation. A variation of ±30 µm in height change due to bead curvature is therefore adequate depth of focus for marking.

Sitting the beads on a 75 µm diameter aperture there is a mark height change between the largest and smallest beads of a little over 2 µm. Beads protrude through the aperture between 0 µm (at the aperture edge) and 3.9 µm and 6 µm (at bottom dead centre). The focal plane of the laser may be arranged to be 3 µm below the aperture plane and this ensures that no part of the marked image is more that 3 µm off focus. (Assuming that the marking radiation is brought to a flat field focus.)

A focal depth of 3 µm is achievable and seems commensurate with production of 5 µm features.

The invention has been described by way of examples only and variation, may be made to them without departing from the scope of the invention.

Maximum ratio 1.2
Minimum ratio 0.8

| Bead radius | Aperture radius | Protrusion nominal | Protrusion 110% bead | Protrusion 90% bead | Figure of merit | Bead radius | Aperture radius | Protrusion nominal | Protrusion 110% bead | Protrustion 90% bead | Figure of merit |
|---|---|---|---|---|---|---|---|---|---|---|---|
| 1 | 1 | 1 | 0.536675042 | #NUMI | #NUMI | 1 | 0.5 | 0.1339746 | 0.10912879 | 0.1755002 | 6.02669116 |
| 1 | 0.99 | 0.85893264 | 0.521840727 | #NUMI | #NUMI | 1 | 0.49 | 0.12827757 | 0.10460053 | 0.16762353 | 6.34668819 |
| 1 | 0.98 | 0.80100251 | 0.507468412 | #NUMI | #NUMI | 1 | 0.48 | 0.12273151 | 0.10018183 | 0.16 | 6.66893177 |
| 1 | 0.97 | 0.75889508 | 0.493529902 | #NUMI | #NUMI | 1 | 0.47 | 0.11733359 | 0.09587138 | 0.15262067 | 7.04854717 |
| 1 | 0.96 | 0.72 | 0.48 | #NUMI | #NUMI | 1 | 0.46 | 0.11208108 | 0.09166792 | 0.14547727 | 7.43365187 |
| 1 | 0.95 | 0.6877501 | 0.466856085 | #NUMI | #NUMI | 1 | 0.45 | 0.10697145 | 0.08757023 | 0.13856217 | 7.84437616 |
| 1 | 0.94 | 0.65882558 | 0.454077752 | #NUMI | #NUMI | 1 | 0.44 | 0.10200223 | 0.06357714 | 0.13168828 | 8.28309371 |
| 1 | 0.93 | 0.63244048 | 0.44164852 | #NUMI | #NUMI | 1 | 0.43 | 0.09717111 | 0.07968754 | 0.125389 | 8.75245611 |
| 1 | 0.92 | 0.60808164 | 0.429545589 | #NUMI | #NUMI | 1 | 0.42 | 0.0924759 | 0.07590036 | 0.11911822 | 9.25543315 |
| 1 | 0.91 | 0.58539175 | 0.417759828 | #NUMI | #NUMI | 1 | 0.41 | 0.06791448 | 0.07221456 | 0.11305022 | 9.78536005 |
| 1 | 0.9 | 0.56411011 | 0.406274607 | #NUMI | #NUMI | 1 | 0.4 | 0.05348485 | 0.058852915 | 0.10717966 | 10.3759931 |
| 1 | 0.89 | 0.54403948 | 0.395077643 | #NUMI | #NUMI | 1 | 0.39 | 0.07918514 | 0.06514315 | 0.10150161 | 11.0015752 |
| 1 | 0.88 | 0.52502632 | 0.384156878 | #NUMI | #NUMI | 1 | 0.38 | 0.07501351 | 0.06175574 | 0.09601136 | 11.8789141 |
| 1 | 0.87 | 0.50694828 | 0.373501361 | #NUMI | #NUMI | 1 | 0.37 | 0.07096825 | 0.05846594 | 0.09070457 | 12.4074749 |
| 1 | 0.86 | 0.48970597 | 0.363100962 | #NUMI | #NUMI | 1 | 0.36 | 0.0670477 | 0.05527296 | 0.06557716 | 13.1984915 |
| 1 | 0.85 | 0.47321731 | 0.352946283 | #NUMI | #NUMI | 1 | 0.35 | 0.0632503 | 0.05217597 | 0.08082527 | 14.0601 |
| 1 | 0.84 | 0.4574136 | 0.343028589 | #NUMI | #NUMI | 1 | 0.34 | 0.00857458 | 0.04917421 | 0.07564532 | 14.9975006 |
| 1 | 0.83 | 0.44223661 | 0.333339744 | #NUMI | #NUMI | 1 | 0.33 | 0.05601907 | 0.04628863 | 0.07123392 | 16.0211537 |
| 1 | 0.82 | 0.42783648 | 0.323872155 | #NUMI | #NUMI | 1 | 0.32 | 0.05258246 | 0.04345342 | 0.06478789 | 17.1420203 |
| 1 | 0.81 | 0.41357012 | 0.314618725 | #NUMI | #NUMI | 1 | 0.31 | 0.04926344 | 0.04073299 | 0.06250424 | 18.3728566 |
| 1 | 0.8 | 0.4 | 0.305572809 | 0.8 | 0.80901689 | 1 | 0.3 | 0.0480608 | 0.036105 | 0.05838015 | 19.728579 |
| 1 | 0.79 | 0.36689316 | 0.296726189 | 0.673904798 | 1.060511 | 1 | 0.29 | 0.04297335 | 0.03556881 | 0.05441298 | 21.2267191 |
| 1 | 0.78 | 0.37422049 | 0.266078851 | 0.622236112 | 1.19704153 | 1 | 0.28 | 0.04 | 0.03312383 | 0.05060024 | 22.8879934 |
| 1 | 0.77 | 0.36195611 | 0.279619544 | 0.582974658 | 1.31858708 | 1 | 0.27 | 0.03713968 | 0.03078948 | 0.04683958 | 24.7370243 |
| 1 | 0.76 | 0.35007683 | 0.271345059 | 0.55020008 | 1.43443714 | 1 | 0.26 | 0.03439138 | 0.02850523 | 0.04342879 | 26.8032581 |
| 1 | 0.75 | 0.33858217 | 0.2632503 | 0.521611782 | 1.5482184 | 1 | 0.25 | 0.03175416 | 0.02833054 | 0.04005579 | 29.1221455 |
| 1 | 0.74 | 0.52738313 | 0.255330746 | 0.498026317 | 1.66185027 | 1 | 0.24 | 0.02922711 | 0.02424492 | 0.03684964 | 31.7366735 |
| 1 | 0.73 | 0.31655286 | 0.247582025 | 0.472736837 | 1.77654121 | 1 | 0.23 | 0.28680937 | 0.0222479 | 0.03377549 | 34.6983725 |
| 1 | 0.72 | 0.30802594 | 0.24 | 0.451268085 | 1.89314982 | 1 | 0.22 | 0.02450013 | 0.02033903 | 0.03064482 | 36.0749774 |
| 1 | 0.71 | 0.29579832 | 0.232580753 | 0.431353628 | 2.01234498 | 1 | 0.21 | 0.02229851 | 0.01851788 | 0.02805441 | 41.9439948 |
| 1 | 0.7 | 0.28585715 | 0.225320566 | 0.412701685 | 2.13468701 | 1 | 0.2 | 0.0202041 | 0.01678404 | 0.02540333 | 46.4075488 |
| 1 | 0.69 | 0.27619083 | 0.21821591 | 0.39515435 | 2.26067325 | 1 | 0.19 | 0.01821591 | 1.101513714 | 0.02288997 | 51.5940601 |
| 1 | 0.68 | 0.26678780 | 0.211263432 | 0.37857385 | 2.39076586 | 1 | 0.18 | 0.01633339 | 0.0135788 | 0.02051299 | 57.688587 |
| 1 | 0.67 | 0.2578389 | 0.204459946 | 0.36265014 | 2.52540886 | 1 | 0.17 | 0.01455594 | 0.0121027 | 0.01827115 | 64.8461258 |
| 1 | 0.66 | 0.2487344 | 0.197802415 | 0.347893818 | 2.66504271 | 1 | 0.16 | 0.01288299 | 0.0107145 | 0.01616328 | 73.4109005 |
| 1 | 0.65 | 0.24006579 | 0.19128795 | 0.333631047 | 2.81011168 | 1 | 0.15 | 0.011314 | 0.00941191 | 0.01418832 | 63.7449446 |
| 1 | 0.64 | 0.23162509 | 0.184913797 | 0.32 | 2.96107219 | 1 | 0.14 | 0.0088485 | 0.00619465 | 0.01234525 | 96.3714572 |
| 1 | 0.63 | 0.22340467 | 0.178577328 | 0.306948279 | 3.11839897 | 1 | 0.13 | 0.00648601 | 0.00706245 | 0.01063317 | 112.022354 |
| 1 | 0.62 | 0.21539819 | 0.172576037 | 0.294431014 | 3.28259059 | 1 | 0.12 | 0.00722611 | 0.00601508 | 0.0090512 | 131.748788 |
| 1 | 0.61 | 0.20759859 | 0.166607529 | 0.262409428 | 3.45417477 | 1 | 0.11 | 0.00606841 | 0.0050523 | 0.007598589 | 157.091657 |
| 1 | 0.6 | 0.2 | 0.160769515 | 0.270649738 | 3.63371359 | 1 | 0.1 | 0.00501256 | 0.00417393 | 0.00627461 | 190.414443 |
| 1 | 0.59 | 0.19259678 | 0.15505981 | 0.259722294 | 3.8218088 | 1 | 0.09 | 0.00405823 | 0.00337975 | 0.00507862 | 235.451905 |
| 1 | 0.58 | 0.18538353 | 0.149476321 | 0.249000907 | 4.01910738 | 1 | 0.08 | 0.00320514 | 0.00268964 | 0.00401055 | 298.415247 |
| 1 | 0.57 | 0.17835531 | 0.144017045 | 0.238662312 | 4.22630751 | 1 | 0.07 | 0.00245301 | 0.00204341 | 0.00306838 | 390.252316 |
| 1 | 0.56 | 0.17150739 | 0.136680067 | 0.228685726 | 4.44416502 | 1 | 0.06 | 0.00180162 | 0.00150094 | 0.00225317 | 531.749203 |
| 1 | 0.55 | 0.16483535 | 0.13346355 | 0.219052498 | 4.67350058 | 1 | 0.05 | 0.00125078 | 0.00104212 | 0.00156403 | 766.416114 |
| 1 | 0.54 | 0.15833498 | 0.128365734 | 0.209745817 | 4.91520754 | 1 | 0.04 | 0.00080032 | 0.00066685 | 0.00100063 | 1198.41631 |
| 1 | 0.53 | 0.15200236 | 0.123384934 | 0.200750469 | 5.17026068 | 1 | 0.03 | 0.0004501 | 0.00037508 | 0.0005627 | 2131.7498 |
| 1 | 0.52 | 0.14583374 | 0.118519533 | 0.192052634 | 5.4397271 | 1 | 0.02 | 0.00020002 | 0.00016668 | 0.00025004 | 4798.41658 |
| 1 | 0.51 | 0.1398256 | 0.119767981 | 0.18639716 | 5.72477553 | 1 | 0.01 | 5.0001E−05 | 4.1667E−05 | 6.2502E−05 | 19198.4166 |

What is claimed is:

1. An apparatus for locating a plurality of articles to be marked comprising: a support plate having a plurality of apertures extending from a first surface of the plate to a second surface of the plate, the apertures being dimensioned to receive said articles at the first surface so that at least a portion of the articles is presented to be marked from the second surface of the plate; characterised in that the diameter of each aperture is less than 200 μm.

2. An apparatus according to claim 1 wherein substantially tapered sidewalls define the apertures.

3. An apparatus according to claim 2 wherein the angle of the taper of the apertures is adapted so that substantially similar projections of articles protrude through the apertures.

4. An apparatus according to claim 1 wherein the support plate is substantially planar.

5. An apparatus according to claim 1 wherein the diameter of the apertures is less than 100 μm.

6. An apparatus according to claim 1 wherein a placement means is provided for placing articles onto the support plate, the plate being displaceable with respect to the placement means and a discharging means is provided for releasing the articles at a predetermined instant.

7. An apparatus according to claim 6 wherein the discharging means includes an air jet.

8. Apparatus according to claim 6 wherein the discharging means includes a vacuum pump.

9. Apparatus according to claim 6 wherein the discharging means includes an electrostatic generator.

10. Apparatus according to claim 6 wherein the discharging means includes a vibrational device.

11. An apparatus according to claim 1 including a laser which in use is directed towards that portion of the article presented from the second surface of the support plate.

12. An apparatus for locating a plurality of articles comprising: a support plate having a plurality of apertures extending from a first surface of the plate to a second surface of the plate, the apertures being dimensioned to receive said articles at the first surface so that at least a portion of the articles is presented to be viewed from the second surface of the plate, wherein the diameter of each aperture is less than 200 µm and wherein, in use, the articles are disposed between the support plate and a deformable layer, the layer being situated so as to restrict movement of said articles.

13. An apparatus according to claim 12 wherein a force is applied to the layer so as to restrict movement of said articles.

14. A method of marking articles comprising the steps of: placing a plurality of articles on a support plate having a plurality of apertures extending from a first surface of the plate to a second surface of the plate, the apertures having a diameter less than 200 µm and being dimensioned to receive said articles at the first surface so that at least a portion of the articles is presented from the second surface of the plate; marking said portion of the articles presented from the second surface of the plate.

15. A method according to claim 14 wherein said marking step is effected using a laser.

16. A method according to claim 14 further comprising the step of discharging the articles from the support plate after marking of the articles.

* * * * *